US011471701B2

(12) United States Patent
Lim et al.

(10) Patent No.: US 11,471,701 B2
(45) Date of Patent: Oct. 18, 2022

(54) BODY-INSERTABLE DEVICE HAVING ADJUSTABLE RADIATION EMISSION DIRECTION AND RADIATION EMISSION RANGE

(71) Applicant: NATIONAL CANCER CENTER, Goyang-si (KR)

(72) Inventors: Young Kyung Lim, Paju-si (KR); Ui Jung Hwang, Goyang-si (KR); Young Moon Goh, Goyang-si (KR); Hak Soo Kim, Goyang-si (KR); Dong Ho Shin, Suwon-si (KR); Se Byeong Lee, Goyang-si (KR); Jong Hwi Jeong, Seoul (KR); Joo Young Kim, Seoul (KR); Tae Hyun Kim, Seoul (KR)

(73) Assignee: NATIONAL CANCER CENTER, Goyang-si (KR)

(*) Notice: Subject to any disclaimer, the term of this patent is extended or adjusted under 35 U.S.C. 154(b) by 330 days.

(21) Appl. No.: 16/753,138

(22) PCT Filed: Aug. 27, 2018

(86) PCT No.: PCT/KR2018/009854
§ 371 (c)(1),
(2) Date: Apr. 2, 2020

(87) PCT Pub. No.: WO2019/083145
PCT Pub. Date: May 2, 2019

(65) Prior Publication Data
US 2020/0246634 A1    Aug. 6, 2020

(30) Foreign Application Priority Data

Oct. 24, 2017  (KR) .......................... 10-2017-0138194

(51) Int. Cl.
*A61N 5/10* (2006.01)

(52) U.S. Cl.
CPC .... *A61N 5/1007* (2013.01); *A61N 2005/1094* (2013.01)

(58) Field of Classification Search
CPC .... A61N 2005/1094; A61N 2005/1005; A61N 5/1002; A61N 5/1014; A61N 5/1015;
(Continued)

(56) References Cited

U.S. PATENT DOCUMENTS 5,354,257 A    10/1994 Roubin et al.
5,484,384 A    1/1996 Fearnot
(Continued)

FOREIGN PATENT DOCUMENTS

JP    2000-500040 A    1/2000
JP    2001-522667 A    11/2001
(Continued)

OTHER PUBLICATIONS

International Search Report dated Nov. 30, 2018 in PCT/KR2018/009854 filed on Aug. 27, 2018, 2 pages.
(Continued)

*Primary Examiner* — Samuel G Gilbert
(74) *Attorney, Agent, or Firm* — Oblon, McClelland, Maier & Neustadt, L.L.P.

(57) ABSTRACT

A body-insertable device having an adjustable radiation emission direction and radiation emission range, which includes a first outer body extending to be long and an accommodation space having a first accommodation space and a second accommodation space having different distances to the first outer body.

13 Claims, 23 Drawing Sheets

(58) Field of Classification Search
CPC .......... A61N 5/1007; A61N 2005/1024; A61N 2005/1019
USPC ...................................................... 600/3, 6–8
See application file for complete search history.

(56) References Cited

U.S. PATENT DOCUMENTS

| | | |
|---|---|---|
| 5,833,593 A | 11/1998 | Liprie |
| 6,048,299 A | 4/2000 | Hoffmann |
| 6,059,713 A | 5/2000 | Urick et al. |
| 6,110,097 A | 8/2000 | Hastings et al. |
| 6,117,065 A | 9/2000 | Hastings et al. |
| 6,540,655 B1 | 4/2003 | Chin et al. |
| 6,676,590 B1 | 1/2004 | Urick et al. |
| 6,910,999 B2 | 6/2005 | Chin et al. |
| 7,686,755 B2 | 3/2010 | Smith et al. |
| 7,749,149 B2 | 7/2010 | Chin et al. |
| 7,901,345 B2 | 3/2011 | Chin et al. |
| 2005/0185765 A1 | 8/2005 | Chin et al. |
| 2005/0261541 A1* | 11/2005 | Henderson ............ A61N 5/1027 600/7 |
| 2008/0009658 A1 | 1/2008 | Smith et al. |
| 2008/0214887 A1* | 9/2008 | Heanue ................ A61N 5/1014 600/3 |
| 2010/0152521 A1 | 6/2010 | Price |
| 2011/0257459 A1* | 10/2011 | Sutton ............... A61M 37/0069 600/7 |
| 2014/0257092 A1 | 9/2014 | Lamoureux et al. |
| 2018/0318603 A1* | 11/2018 | Park ..................... A61N 5/1039 |

FOREIGN PATENT DOCUMENTS

| | | |
|---|---|---|
| JP | 2001-525233 A | 12/2001 |
| JP | 2014-528285 A | 10/2014 |
| KR | 10-2009-0074145 A | 7/2009 |
| KR | 10-2013-0056624 A | 5/2013 |
| KR | 10-1840565 B1 | 3/2018 |
| WO | WO 99/29370 A1 | 6/1999 |
| WO | WO 2007/149363 A2 | 12/2007 |
| WO | WO 2015/023307 A1 | 2/2015 |

OTHER PUBLICATIONS

Japanese Office Action dated Feb. 8, 2021 in Japanese Patent Application No. 2020-522950, 2 pages.

* cited by examiner

BODY-INSERTABLE DEVICE HAVING ADJUSTABLE RADIATION EMISSION DIRECTION AND RADIATION EMISSION RANGE

TECHNICAL FIELD

The present invention relates to an insertable device, and more particularly, to a body-insertable device for brachytherapy.

BACKGROUND ART

Radiation therapy for cancer patients may be largely classified into two types: external beam radiation therapy where radiation is delivered to a tumor from a radiation source placed outside a patient's body, and brachytherapy where radiation is delivered from a radiation source placed inside a patient's body.

Between them, the brachytherapy is carried out by inserting the radiation source into a tumor, and this therapy has an advantage in that although a high radiation dose is delivered to the tumor, the radiation dose transmitted to surrounding healthy organs can be reduced significantly.

In the brachytherapy, radiation is emitted by moving the radiation source through an insertable device being inserted into a human body, but there is a problem in that the technology for adjusting the three-dimensional radiation intensity by adjusting the radiation emission direction and the radiation emission range in the insertable device has not been developed to a sufficient level.

In particular, when it is necessary to use a bent insertable device for the radiation emission on a tumor located in a region such as uterine cancer, it is difficult to provide an insertable device with an intensity adjusting function.

DISCLOSURE

Technical Problem

Therefore, an object of the present invention is to provide an insertable device for brachytherapy, which, while being in a bent shape, is able to adjust the radiation intensity.

Technical Solution

The above object of the present invention can be achieved by an insertable device, which includes: an outer body including a first outer body extending in a long manner, a second outer body extending in a long manner, and a bent part for connecting the first outer body and the second outer body such that the first outer body and the second outer body are bent; a first inner body positioned inside the first outer body and having an accommodation space in which a radiation source is accommodated; a second inner body positioned inside the second outer body, having a guide space enabling the radiation source to pass therethrough and being capable of operating rotation thereof, and an inner connection part positioned in correspondence to the bent part inside the outer body, has a connection space communicating with the guide space and the accommodation space such that the radiation source is able to pass therethrough, and connects the first inner body and the second inner body, wherein the accommodation space includes a first accommodation space and a second accommodation space having different distances from the first outer body, and the first inner body is separated from the first outer body and rotated by the rotation of the second inner body.

The first accommodation space and the second accommodation space may be formed in a long manner along the first inner body.

The accommodation space may be formed in a trench form in the first inner body.

The insertable device may further include an accommodation space partitioning member positioned within the accommodation space, and the first accommodation space and the second accommodation space may be separated by the accommodation space partitioning member.

The inner connection part may include a rotation power mechanism.

The rotation power mechanism may include at least one among a flexible shaft, a bellows, and a joint.

One end of the inner connection part may be fixed to the first inner body, and the other end of the inner connection part may be connected to the second inner body.

The first inner body may consist of a material which has greater radiation shielding performance than that of the first outer body.

The guide space may include a first guide space and a second guide space that are separated from each other, and may further include: a first accommodation guide which connects the first guide space to any one of the first accommodation space and the second accommodation space within the connection space; and a second accommodation guide which connects the first guide space to the other of the first accommodation space and the second accommodation space within the connection space.

The first accommodation guide and the second accommodation guide may be in a tube shape through which a radiation source is able to pass.

The first accommodation guide and the second accommodation guide may be positioned on the periphery of the inner connection part; and the first accommodation guide may be connected to either the first accommodation space or the second accommodation space, which is positioned farther from the first guide space.

The inner connection part may have a connection space inside; at least part of each of the first accommodation guide and the second accommodation guide may be positioned within the connection space; and the first accommodation guide may be connected to either the first accommodation space or the second accommodation space, which is positioned closer to the first guide space.

The object of the present invention is achieved by an insertable device, which includes an outer body extended lengthwise; an inner body, which is positioned inside the outer body and has an accommodation space in which a radiation source is accommodated; wherein the accommodation space includes a first accommodation space and a second accommodation space having different distances from the first outer body, and the inner body is separated from the outer body and rotated.

The first accommodation space and the second accommodation space may be formed lengthwise along the inner body.

The accommodation space may be formed in a trench form in the inner body.

The insertable device may further include an accommodation space partitioning member positioned within the accommodation space, and the first accommodation space and the second accommodation space may be separated by the accommodation space partitioning member.

The inner body may consist of a material which has greater radiation shielding performance than that of the first outer body.

Advantageous Effects

According to the present invention, there is provided an insertable device for brachytherapy, which, while being in a bent shape, is able to adjust radiation intensity.

MODE FOR INVENTION

Hereinafter, the present invention will be described in more detail with reference to the accompanying drawings.

The accompanying drawings are only examples as illustrated in order to explain the technical idea of the present invention in more detail, and thus the spirit of the present invention is not limited to the accompanying drawings. The accompanying drawings may be exaggerated for explanation with regard to the thickness, length, etc. of each part. In the present invention, the adjustment of the 'intensity of the radiation' is performed by a method of adjusting the position and time where and when a radiation source stays, and a method of adjusting the radiation emission direction and/or the radiation emission range.

The insertable device according to a first embodiment of the present invention will be described with reference to FIGS. 1 to 8.

Figure 1:
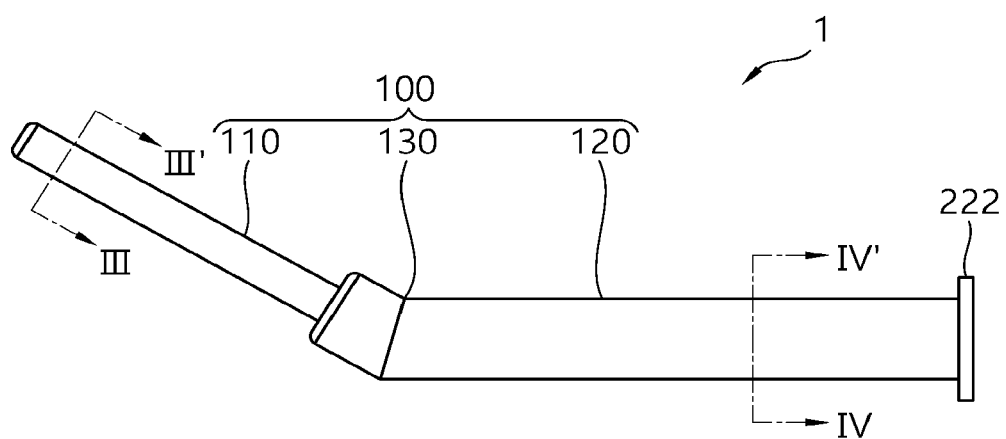
FIG. 1 is a perspective view of an insertable device according to a first embodiment of the present invention.
Figure 2:
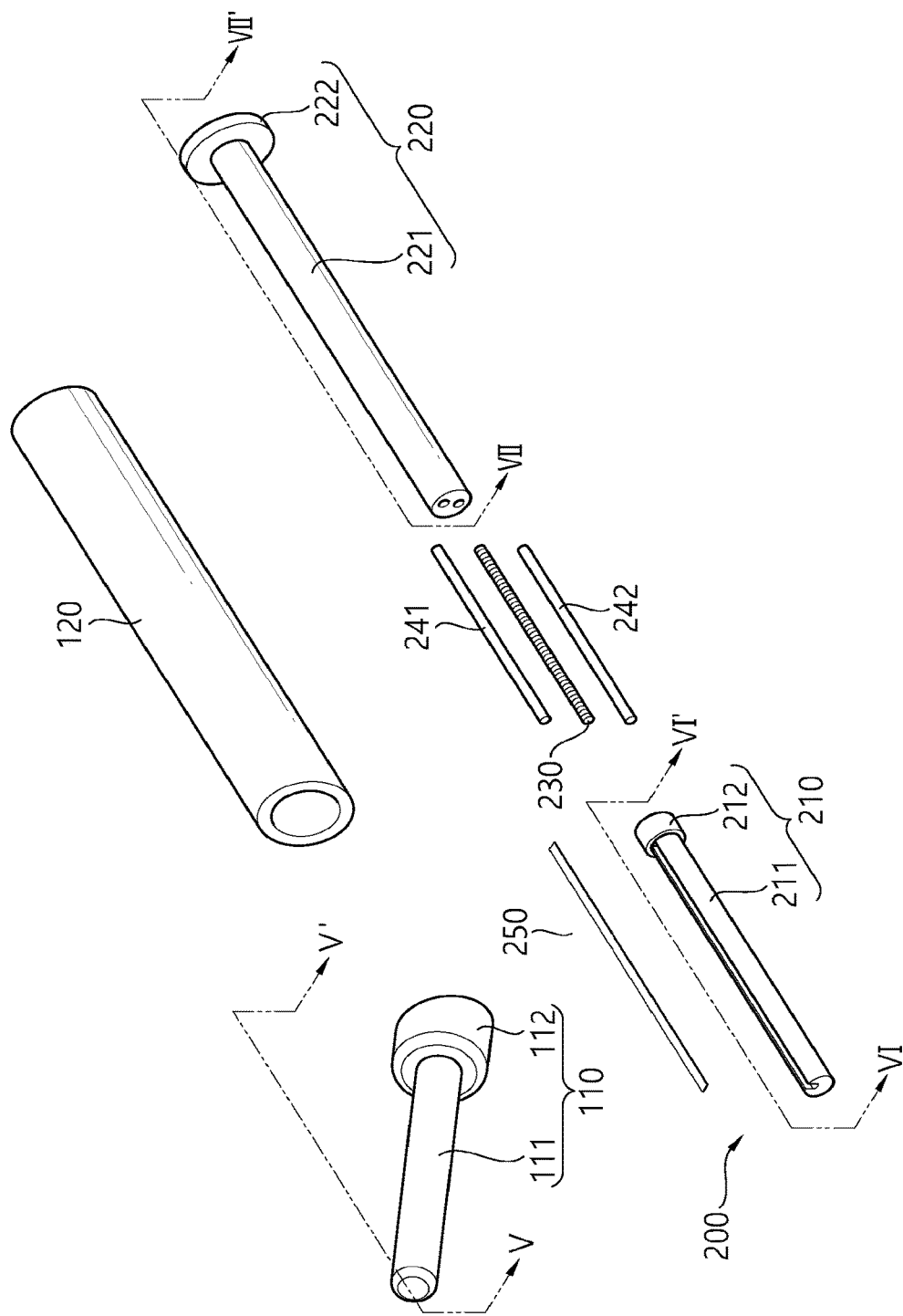
FIG. 2 is an exploded perspective view of an insertable device according to a first embodiment of the present invention.
Figure 3:
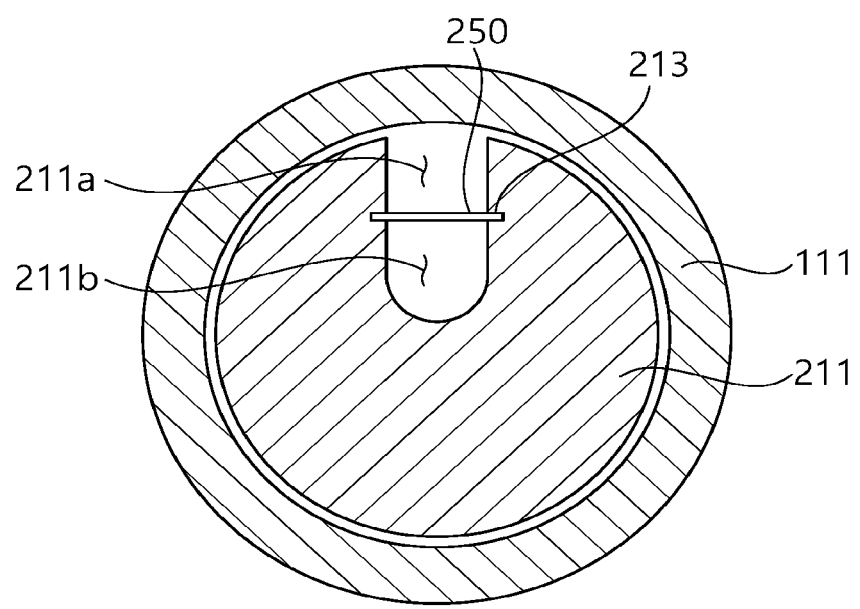
FIG. 3 is a cross-sectional view taken along the III-III' line of FIG. 1.
Figure 4:
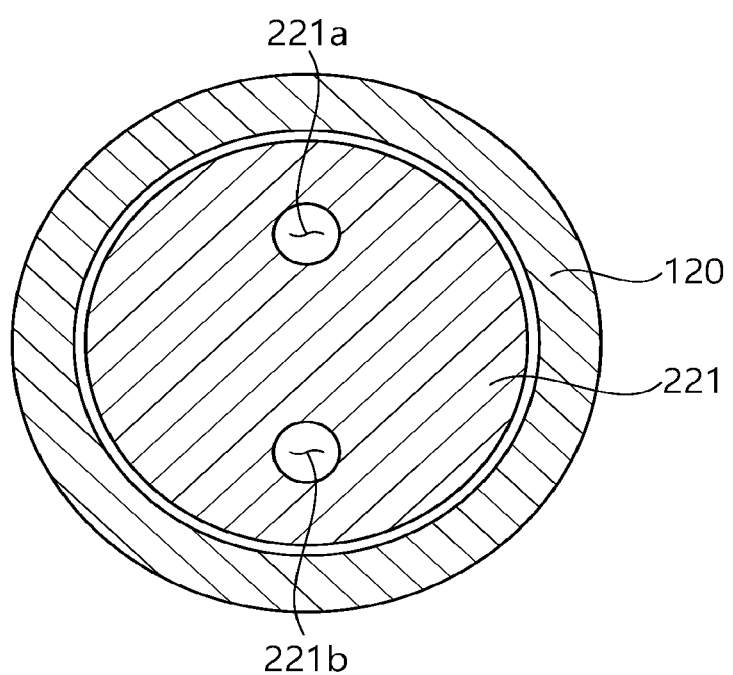
FIG. 4 is a cross-sectional view taken along the IV-IV' line of FIG. 1.
Figure 5:
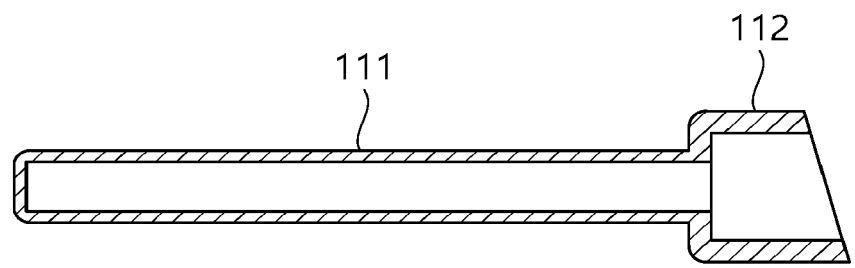
FIG. 5 is a cross-sectional view taken along the V-V' line of FIG. 2.
Figure 6:
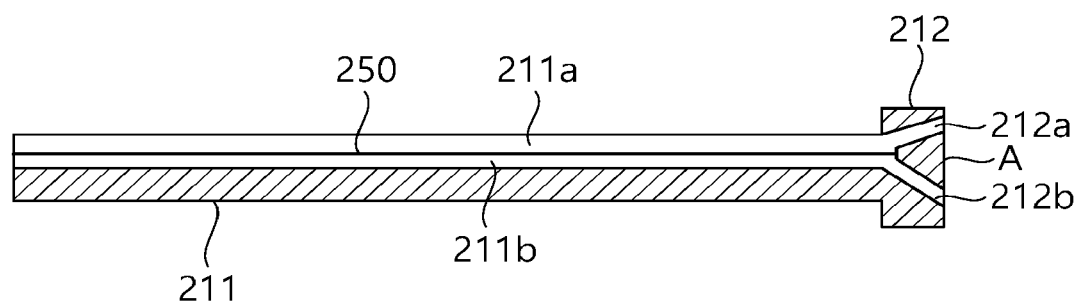
FIG. 6 is a cross-sectional view taken along the VI-VI' line of FIG. 2.
Figure 7:
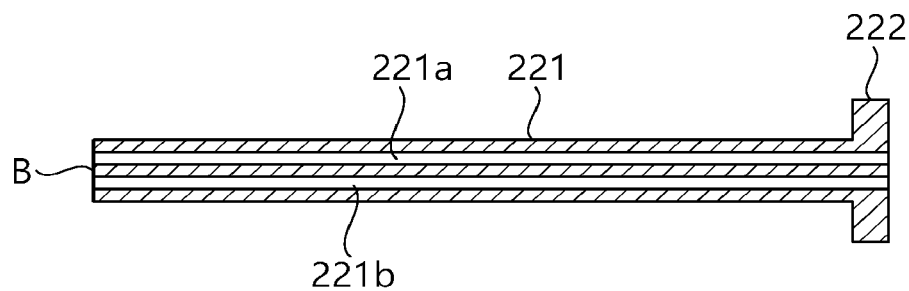
FIG. 7 is a cross-sectional view taken along the VII-VII' line of FIG. 2.
Figure 8:
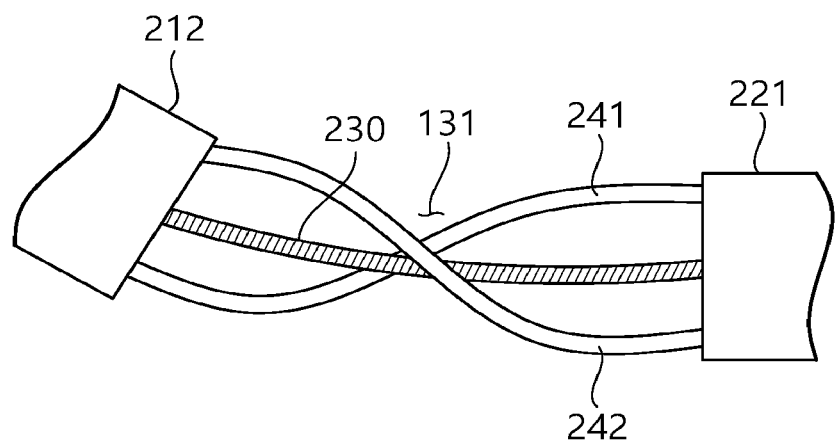
FIG. 8 is a schematic diagram for explanation of the connection between a first inner body and a second inner body in an insertable device according to a first embodiment of the present invention.

FIG. 1 is a perspective view of an insertable device according to a first embodiment of the present invention; FIG. 2 is an exploded perspective view of an insertable device according to a first embodiment of the present invention; FIG. 3 is a cross-sectional view taken along the III-III' line of FIG. 1; FIG. 4 is a cross-sectional view taken along the IV-IV' line of FIG. 1; FIG. 5 is a cross-sectional view taken along the V-V' line of FIG. 2; FIG. 6 is a cross-sectional view taken along the VI-VI' line of FIG. 2; FIG. 7 is a cross-sectional view taken along the VII-VII' line of FIG. 2; and FIG. 8 is a schematic diagram for explanation of the connection between first inner body and a second inner body in an insertable device according to a first embodiment of the present invention.

An insertable device 1 according to a first embodiment largely consists of an outer body 100 and an inner body 200.

The outer body 100 forms the entire exterior and accommodates the inner body 200 in an empty space inside. In a first embodiment, an operator 222 of the inner body 200 is exposed to the outside of the outer body 100.

The outer body 100 overall has a thin and long shape and is bent. Specifically, the outer body 100 includes a first outer body 110, a second outer body 120, and a bent part 130, and the first outer body 110 and the second body 120 are connected to be bent by the bent part 130.

As shown in FIG. 5, the first outer body 110 includes a thin and long first part 111 and a second part 112 with an expanded diameter. The second outer body 120 is provided in a cylindrical shape with a constant diameter.

The outer body 100 as such may be provided in various manners. The outer body 100 may be provided as an overall integrated body or may be provided such that the first outer body 110 and the second outer body 120 are manufactured individually and then coupled thereto by welding, press fitting or like. In addition, the outer body 100 may be provided in such a form that the first outer body 110 and/or the second outer body 120 are manufactured as a plurality of parts and coupled to each other. Alternatively, the bent part 130 may also be manufactured individually and then the first outer body 110, the second outer body 120, and the bent part 130 may be coupled by a method such as welding, press fitting, etc.

Meanwhile, in another embodiment, the first outer body 110 and the second outer body 120 may be provided to be adjustable without fixing the degree of bending, (I.e., angle of bending).

Both the first outer body 110 and the second outer body 120 are provided such that their vertical cross sections in a lengthwise direction are in a circular shape, and their cross sections of an inner space thereof are also in a circular shape. The first outer body 110 shows a change in its cross-sectional area according to the orientation of the lengthwise direction, and overall, the cross-sectional area of the second outer body 120 is greater than that of the first outer body 110. In another embodiment, the cross sections of the first outer body 110 and/or the second outer body 120 may be in an elliptical shape, etc. rather than a circular shape.

The first outer body 110 of the outer body 100 is primarily brought into contact or close to a treatment target (tumor or the like), and, while the first outer body 110 is brought into contact or close to a treatment target (tumor, etc.), and radiation is emitted toward the treatment target from a radiation source placed in the inner body 200 (see FIGS. 11a to 11d). The first outer body 110 may be made of a metallic material with a low atomic number (e.g., titanium) or a non-metallic material (e.g., plastic).

Part of the second outer body 120 is inserted into the human body and the other part is exposed to the outside. The second outer body 120 may be made of a metallic material (e.g., stainless steel) or a non-metallic material (e.g., plastic).

The inner body 200 includes a first inner body 210, a second inner body 220, an inner connection part 230, a first accommodation guide 241, a second accommodation guide 242, and an accommodation space partitioning member 250.

The first inner body 210 includes a first part 211 which is extended lengthwise and a second part 212 with an increased width.

As illustrated in FIGS. 3 and 6, a first accommodation space 211a and a second accommodation space 211b, which are extended lengthwise along the longitudinal direction, are formed in the first part 211 of the first inner body 210. A first guide part 212a and a second guide part 212b are formed in the second part 212 of the first inner body 210. The first guide part 212a is connected to the first accommodation space 211a, and the second guide part 212b is connected to the second accommodation space 211b.

The entire accommodation space (211a, 211b) is formed in a trench form. The first accommodation space 211a and the second accommodation space 211b are partitioned by an accommodation space partitioning member 250 and disposed in a vertical direction.

The accommodation space partitioning member 250 is made of a thin plate, and may be made of titanium, but is not limited thereto. The position of the accommodation space partitioning member 250 is fixed by inserting its both ends in the longitudinal direction into a partitioning member receiving groove 213, which is formed lengthwise along the longitudinal direction in the first inner body 210.

Likewise, a first accommodation space 211a and a second accommodation space 211b are disposed to have a different distance from the first outer body 110 and/or from the center of cross-section of the first inner body 210. With regard to the radiation source, the interference between the radiation and the first inner body 210 varies depending on where the radiation source is accommodated between the first accommodation space 211 and the second accommodation space 211b, and accordingly, the emission range of the radiation to be emitted to the outside varies.

In the first embodiment, the cross-section center of the first part 211 of the first inner body 210 is spaced apart from the second accommodation space 211b, which is located at a lower part thereof.

The first guide part 212a and the second guide part 212b are formed to be inclined, and are disposed in a vertical direction with the central region A interposed therebetween when viewed from an end surface of the second part 212.

As illustrated in FIGS. 4 and 7, the second inner body 220 consists of the first part 221 extended lengthwise, and a second part (an operator 222) with an increased width. The operator 222 is exposed to the outside of an end of the outer body 100, and the user changes the radiation emission direction by rotating the operator 222.

A first guide space 221a and a second guide space 221b, which are extended lengthwise along the longitudinal direction, are formed in the second inner body 220. The cross-sections of the first guide space 221a and the second guide space 221b are in a circular shape have a constant diameter.

Looking at the end surface of the first part 221, the first guide space 221a and the second guide space 221b are disposed in a vertical direction with the central region (B region) interposed therebetween.

As illustrated in FIGS. 2 and 8, the first inner body 210 and the second inner body 220 are spaced apart so that there is a connection space 131 corresponding to the bent part 130.

An inner connection part 230, a first accommodation guide 241, and a second accommodation guide 242 are disposed in the connection space 131, which connects the first inner body 210 and the second inner body 220.

The inner connection part 230 connects the central region (A region) of an end face of the second part 212 of the first inner body 210 and the central region (B region) of an end face of a first part 221 of a second inner body 220.

The inner connection part 230 is a rotation power transmitting mechanism between two shafts that cross each other and may be at least one among a flexible shaft, a bellows, or a joint, but the inner connection part 230 is not limited thereto. In particular, the inner connection part 230 may be provided as a pipe-shaped flexible shaft and may be especially made of a high-carbon steel wire and the wire may be in the form of a multiple layer. In the present invention, the inner connection part 230 may be prepared in various shapes as long as it can transmit the rotating motion of the second inner body 220 to the first inner body 210.

The connection between the inner connection part 230 and the inner body (210, 220) may be performed by a method such as welding or brazing.

The guide part (212a, 212b) and the guide space (221a, 221b) are connected by an accommodation guide (241, 242). The accommodation guide (241, 242) has a tube shape with an internal space, and the material may be a metal or a resin, but is not limited thereto.

Specifically, the first accommodation guide 241 connects a second guide part 212b located at a lower part thereof and a first guide space 221a located at an upper part thereof, whereas the second accommodation guide 242 connects a first guide part 212a located at an upper part thereof and a second guide space 221b located at a lower part thereof. This connection by a crossover method is intended to compensate for the difference in path length of a radiation source generated in the bent part 130 by rotation. That is, this connection is to ensure that the entire path length difference due to rotation is not changed, in a case where the radiation source is located at the first accommodation space 211a and in a case where the radiation source is located at the second accommodation space 211b.

The connection between the accommodation guide (241, 242) and the first inner body 210 and the second inner body 220 may be achieved by various methods such as welding, brazing, or adhesion.

Through the connection by a crossover method, as illustrated in FIG. 8, the first accommodation guide 241 and the second accommodation guide 242 are disposed to be twisted together with the inner connection part 230 interposed therebetween.

By the configuration of the inner body 200 described above, when a radiation source is inserted into the first guide space 221a from the outside, it passes through the first accommodation guide 241 and the second guide part 212b, and is located in the second accommodation space 211b, which is located in the central part of the first inner body 210. Additionally, when a radiation source is inserted into the second guide space 221b from the outside, it passes through the second accommodation guide 242 and the first guide part 212a, and is located in the first accommodation space 211a, which is located on the outside of the first inner body 210.

Hereinafter, the adjustment of radiation intensity in the insertable device according to a first embodiment will be described with reference to FIGS. 9 to 12.

Figure 9:
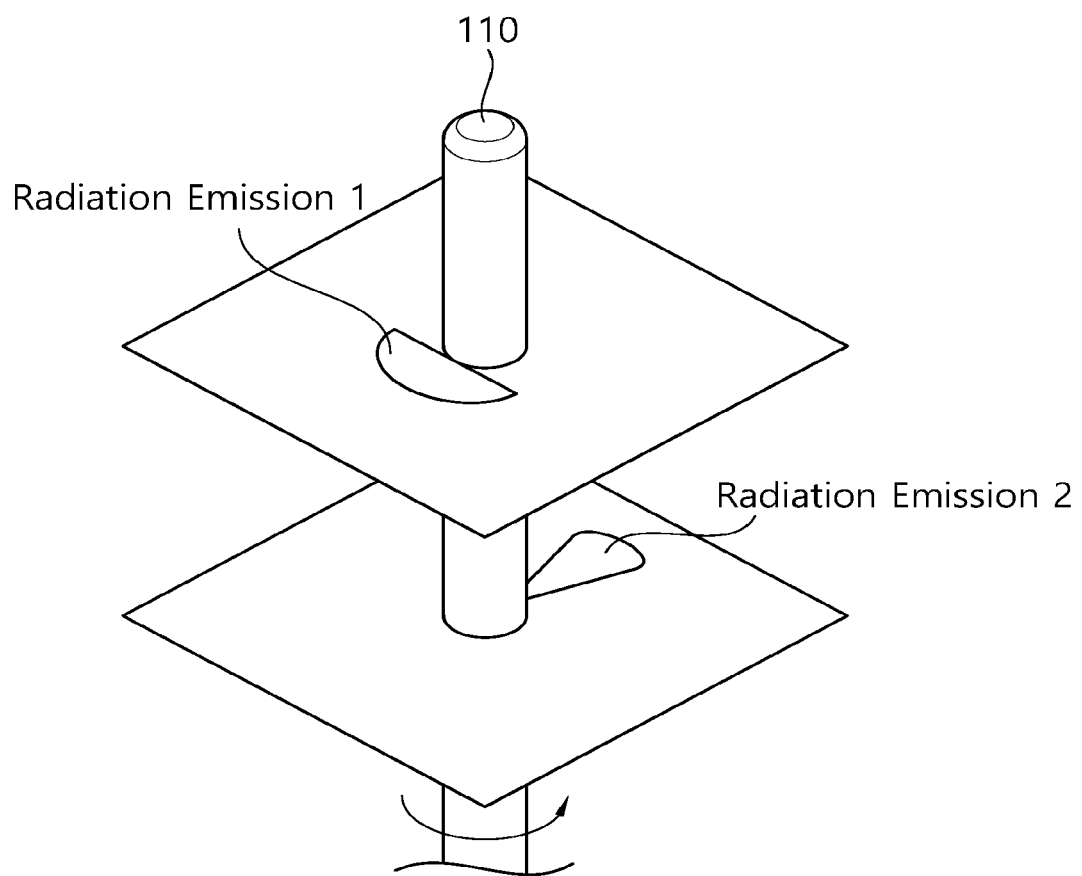
FIG. 9 is a schematic diagram for explanation of the adjustment of radiation intensity according to the rotation of a second inner body in an insertable device according to a first embodiment of the present invention.
Figure 10:
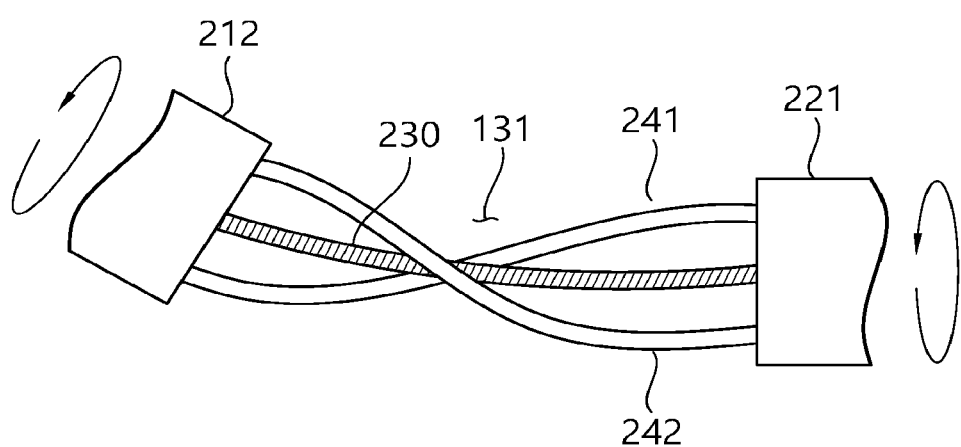
FIG. 10 is a schematic diagram for explaining the rotation of a first inner body according to the rotation of a second inner body in an insertable device according to a first embodiment of the present invention.

FIG. 9 is a schematic diagram for explanation of the adjustment of radiation intensity according to the rotation of a second inner body in an insertable device according to a first embodiment of the present invention; FIG. 10 is a schematic diagram for explaining the rotation of a first inner body according to the rotation of a second inner body in an insertable device according to a first embodiment of the present invention; and FIGS. 11a to 11d and FIG. 12 are schematic diagrams illustrating a change in the position of a radiation source and adjustment of the radiation intensity in an insertable device according to a first embodiment of the present invention.

In the insertable device 1 according to a first embodiment, the emission direction and the emission range of a radiation source may be adjusted by selecting the position for inserting the radiation source and operation of the adjusting unit 222.

As described above, the position of a radiation source in the first inner body 210 is determined according to the selection of the guide space (211a, 221b) when the radiation source is inserted. That is, a radiation source may be located at the central part of the first inner body 210 or may be spaced apart from the center according to the selection of the guide space (221a, 221b). The position of the radiation source in a longitudinal direction within the accommodation space (211a, 211b) can be adjusted variously.

As illustrated in FIG. 8, when an operator 222 exposed to the outside is rotated, the first part 221 of the second inner body 220 rotates. The rotation power of the first part 221 is transmitted to the first inner body 210 by an inner connection part 230, and thereby the first inner body 210 rotates and the position and shape of the second accommodation guide 242 are also changed. The emission direction of a radiation source located in the accommodation space (211a, 211b) is changed by the rotation of the first inner body 210.

By the selection and rotation of the accommodation space (211a, 211b) within the first inner body 210 of a radiation source as described above, the emission direction and the emission range of radiation change as illustrated in FIGS. 11a to 11d.

Figure 11A:
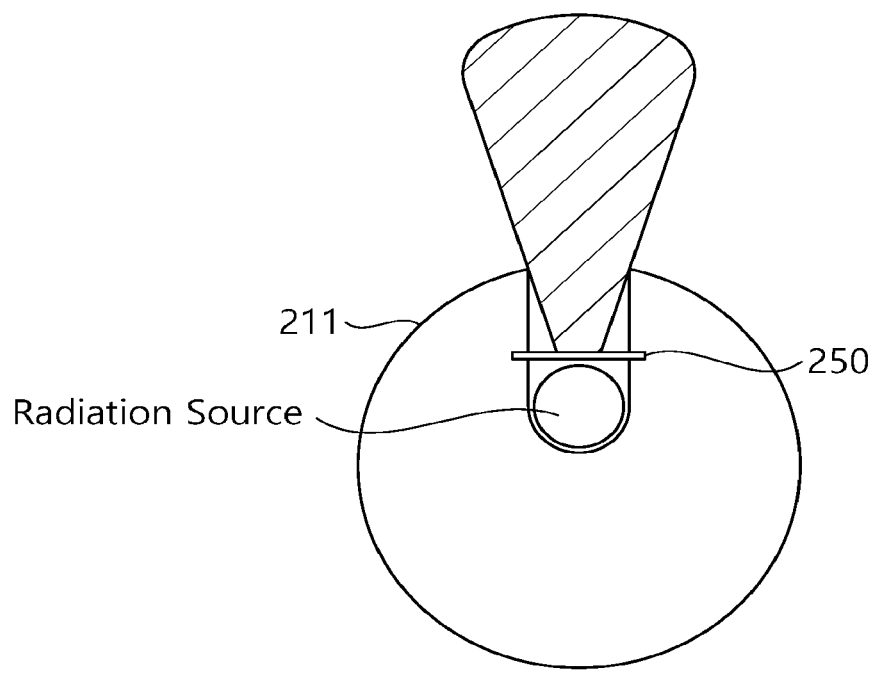
FIGS. 11a to 11d and FIG. 12 are schematic diagrams illustrating a change in the position of a radiation source and adjustment of the radiation intensity in an insertable device according to a first embodiment of the present invention.
Figure 11B:
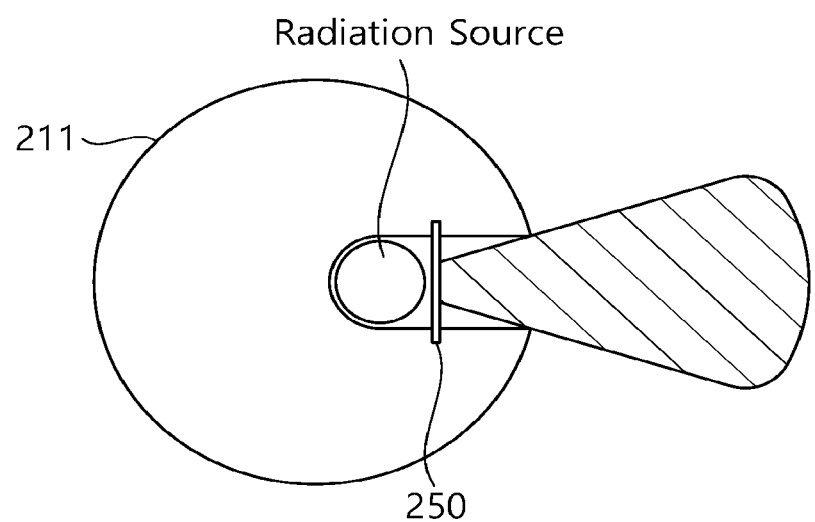
Figure 11C:
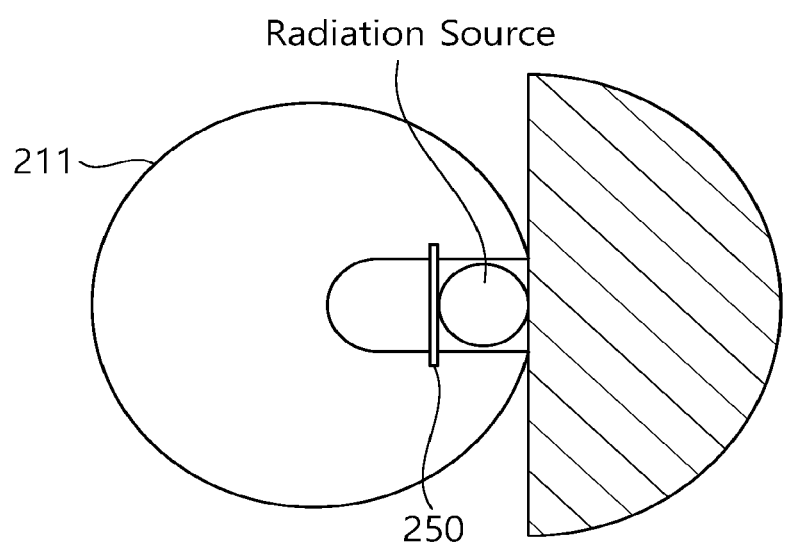
Figure 11D:
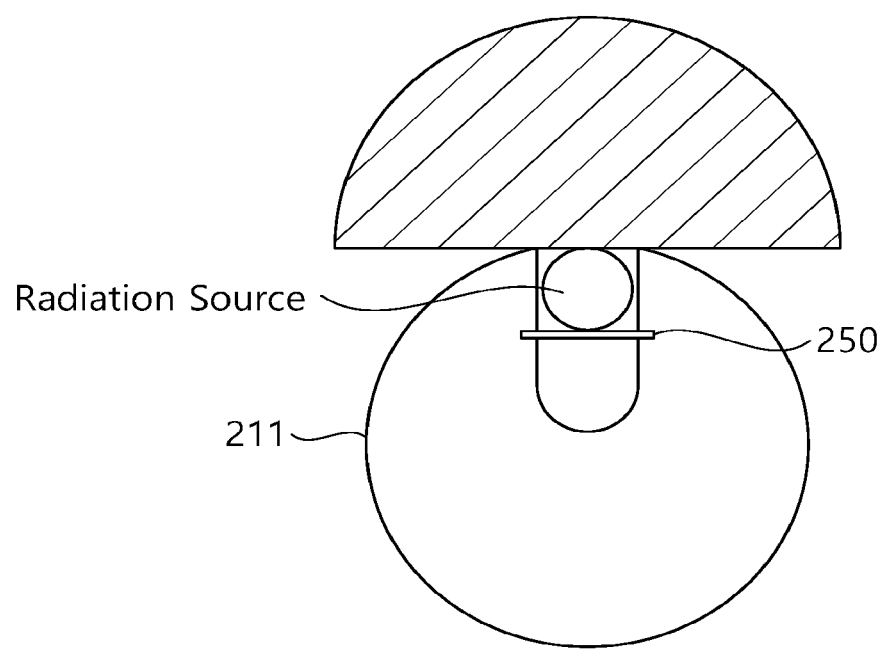

In detail, as illustrated in FIGS. 11a and 11b, the emission direction of radiation can be adjusted by adjusting the rotation of a radiation source. Additionally, as illustrated in FIGS. 11a and 11d, the emission range of radiation can be changed by changing the accommodation space (211a, 211b) of a radiation source. This is explained in more detail as follows.

The radiation from a radiation source is emitted radially. When the radiation source is located in the central part as illustrated in FIG. 11a, the emission angle of the radiation is limited by the first inner body 210 located between the radiation source and the first outer body 110 and thus the radiation has a narrow radiation emission range. In contrast, when the radiation source is located to be spaced apart from the central part as illustrated in FIG. 11d, the emission angle of the radiation limited less by the first inner body 210 and thus the radiation has a wide radiation emission range.

Meanwhile, the radiation in a direction opposite to the radiation emission direction described above is blocked by the thickness of the first inner body 210. The first inner body 210 is made of a material which has greater radiation shielding performance than that of the first outer body 110.

Figure 12:
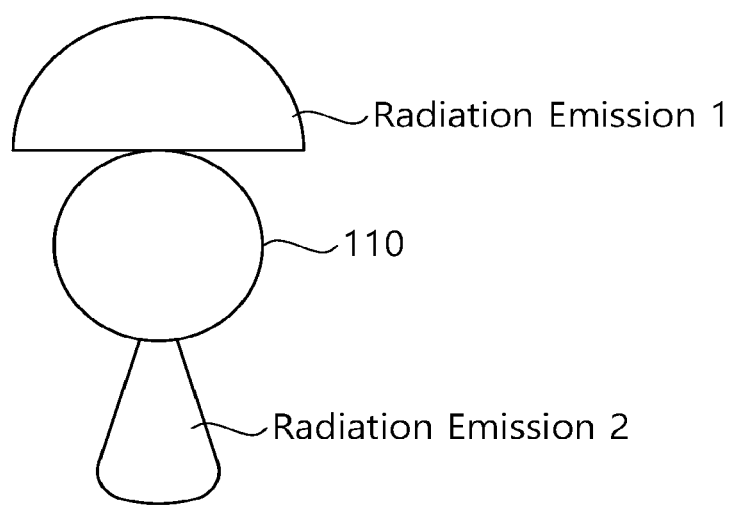

Accordingly, as illustrated in FIG. 12, a radiation distribution can be obtained, in which radiation emission 1 having a wide radiation emission range, and radiation emission 2 having a narrow radiation emission range and emitting radiation to a direction different from that of the radiation emission 1. That is, both the radiation emission direction and the radiation emission range can be adjusted.

Meanwhile, it is certain that the radiation emission direction is not limited to 90 degrees or 180 degrees of angle but can be continuously adjusted, unlike as illustrated in the drawing.

As such, the radiation emission direction is changed in response to the rotation of the operator 222, and the degree of change in the radiation emission direction may be in a range of 10% to 100%, 30% to 100%, 50% to 100%, and 80% to 100% relative to the degree of rotation of the operator 222. In response to the rotation of the operator 222, the radiation emission direction may be rotated by the same angle of the rotation of the operator 222.

The configuration of the operator 222 may be changed in various ways. In another embodiment, the operator 222 may further include an additional device so as to change the ratio of the degree of precision in the radiation emission direction in response to the degree of rotation by the operator 222. In still another embodiment, the operator 222 may be able to rotate the second inner body 220 through an additional configuration connected to the second inner body 220, without being integrally formed with the second inner body 220 or having the operator 222 in the second inner body 220. In still another embodiment, the second inner body 220 may be rotated through an additional mechanical-electrical device.

Brachytherapy can be effectively performed using the insertable device according to the present invention, which will be described with reference to FIG. 13.

After inserting the insertable device 1 into the human body, a radiation source is introduced into the insertable device 1. In a state where the insertion is completed, parts of the operator 222 and the second outer body 120 are exposed to the outside of the human body. In addition, the first outer body 110 is inserted into a position of tumor to fit into a bent structure in the human body. In still another embodiment, after the radiation source is introduced into the insertable device 1, the insertable device 1 may be inserted into the human body.

In this state, based on the shape and position of the tumor found in a previous medical examination, the medical profession adjusts the position, emission direction, emission range of the radiation source according to the longitudinal direction of the first outer body 110. The emission direction of the radiation source is adjusted by adjusting the operator 222, and the emission direction is adjusted by the selection of the guide space (221a, 221b) into which the radiation source is to be inserted.

Figure 13:
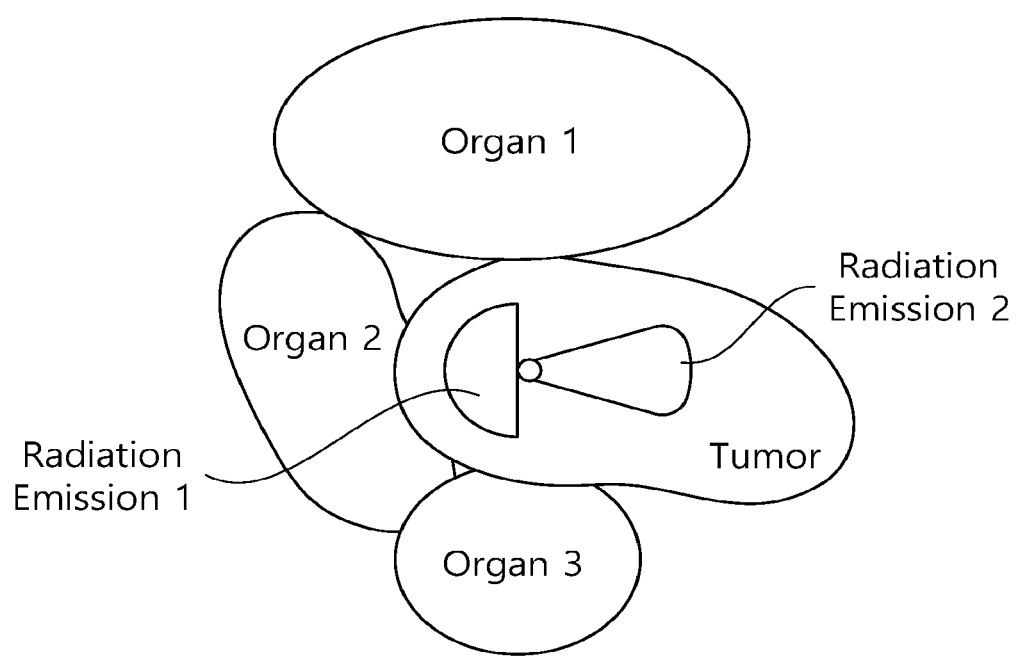
FIG. 13 is a schematic diagram for explaining cancer treatment using an insertable device according to a first embodiment of the present invention.

When the radiation source is positioned with respect to the tumor type as illustrated in FIG. 13, for example, the emission range is widened toward the direction where the tumor is widely distributed with a uniform thickness, thereby minimizing the radiation emission time.

During this treatment process, the radiation emission direction and the radiation emission range can be easily adjusted using the insertable device 1 of the present invention, and through this process, the given dose of a radiation source can be transmitted only to the tumor and simultaneously the treatment time can be significantly reduced.

In the above, the treatment of uterine cancer has been exemplified, however, the insertable device according to the present invention is not limited thereto and can be applied even to head and neck cancer, esophageal cancer, rectal cancer, etc.

Figure 14A:
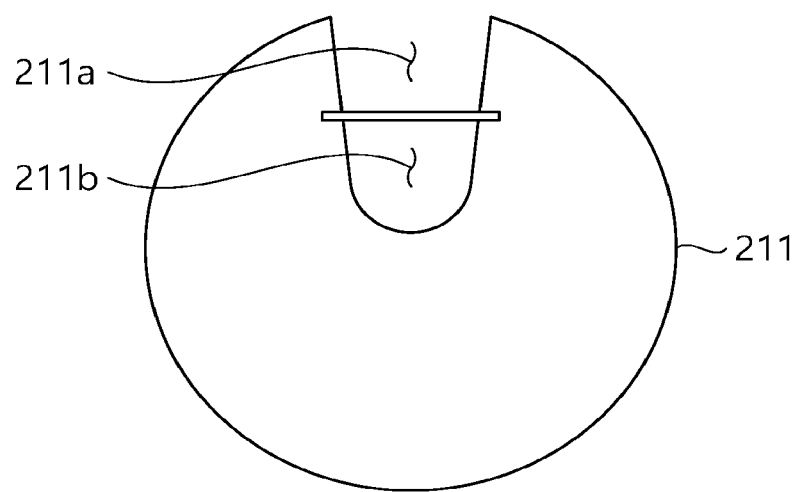
FIGS. 14a and 14b are schematic diagrams illustrating modification examples in an insertable device according to a first embodiment of the present invention.
Figure 14B:
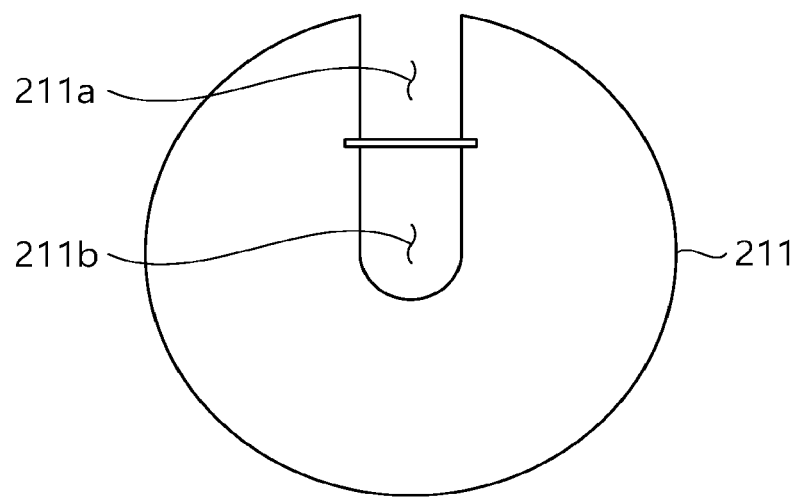

FIGS. 14a and 14b are schematic diagrams illustrating modification examples in an insertable device according to a first embodiment of the present invention.

The first accommodation space 211a and the second accommodation space 211b may be changed in various ways.

As in the modification example illustrated in FIG. 14a, the trench forming the accommodation space (211a, 211b) may be provided so that the width of the trench becomes wider toward the outside. Depending on the shape of the trench, the radiation emission pattern may be changed.

In the modification example illustrated in FIG. 14a, the trench that forms the accommodation space (211a, 211b) is formed to pass through the center of the first inner body 210.

Meanwhile, the accommodation space in the present invention is not limited to two but it may be provided in three or more.

Although not illustrated, the insertable device of the present invention may be formed so that the outer body 100 has no bending. In this case, the outer body 100 may be integrally formed. In this case, the inner body 200 may also be formed without bending, and the inner body 200 may be formed integrally.

The insertable device according to the present invention according to a second embodiment of the present invention will be described with reference to FIGS. 15 and 16.

Figure 15:
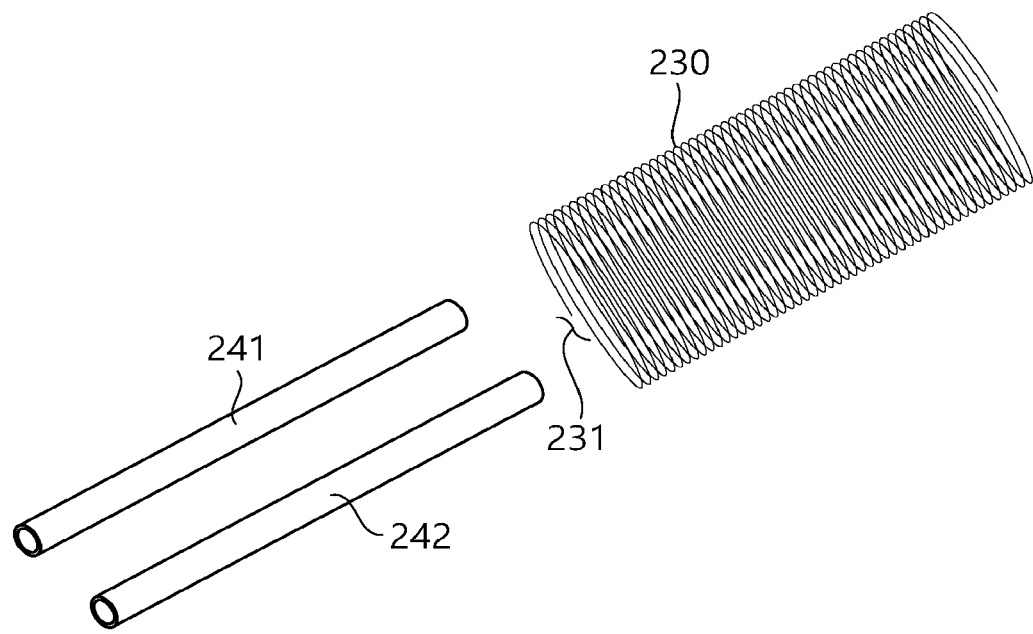
FIG. 15 is a schematic diagram illustrating an inner connection part and an accommodation guide in an insertable device according to a second embodiment of the present invention.
Figure 16:
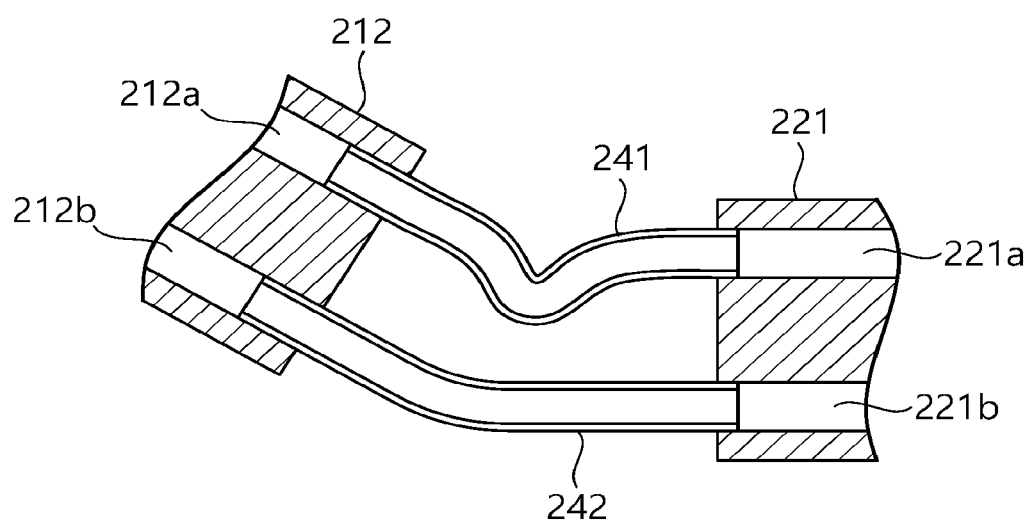
FIG. 16 is a schematic diagram illustrating the connection between a first inner body and a second inner body in an insertable device according to a second embodiment of the present invention.

FIG. 15 is a schematic diagram illustrating an inner connection part and an accommodation guide in an insertable device according to a second embodiment of the present invention; and FIG. 16 is a schematic diagram illustrating the connection between a first inner body and a second inner body in an insertable device according to a second embodiment of the present invention.

In a second embodiment, the diameter of the inner connection part 230 is provided to be larger than that in the first embodiment, and the connection space 231 is present in the connection space 231. The accommodation guide (241, 242) is located within the connection space 231.

The first accommodation guide 241 connects the first guide space 221a located at an upper part thereof and the first guide part 212a located at an upper part thereof, whereas the second accommodation guide 242 connects the second guide space 221b located at a lower part thereof and the second guide part 212b located at a lower part thereof.

That is, in the second embodiment, the connection of the accommodation guide (241, 242) is not in the form of a crossover.

In the second embodiment, in a case where a radiation source is located in the first accommodation space 211a and in a case where a radiation source is located in the second accommodation space 211b, the change in the length of the entire path is allowed to be accommodated within the connection space 231 by a rotation.

The insertable device according to the present invention according to a third embodiment of the present invention will be described with reference to FIGS. 17 to 19.

Figure 17:
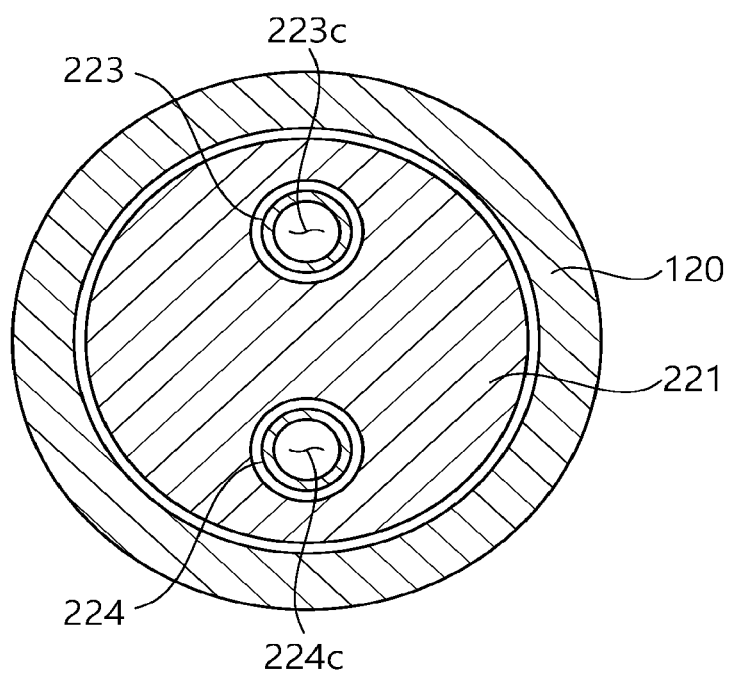
FIGS. 17 and 18 are cross-sectional views of a second outer body and a second inner body in an insertable device according to a third embodiment of the present invention.
Figure 18:
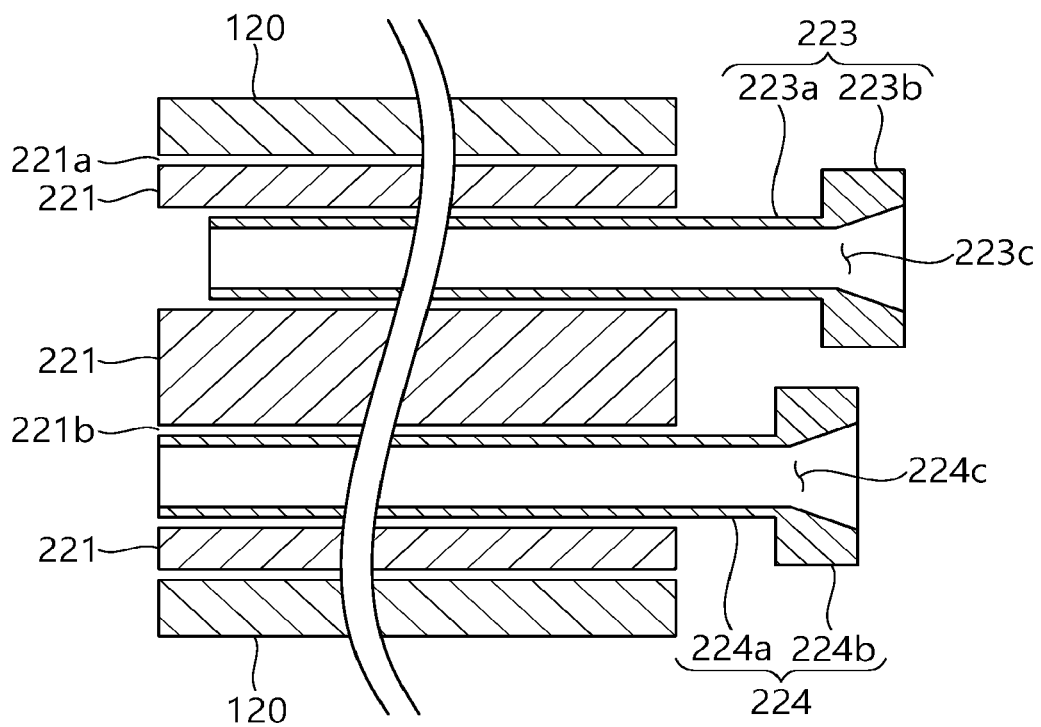
Figure 19:
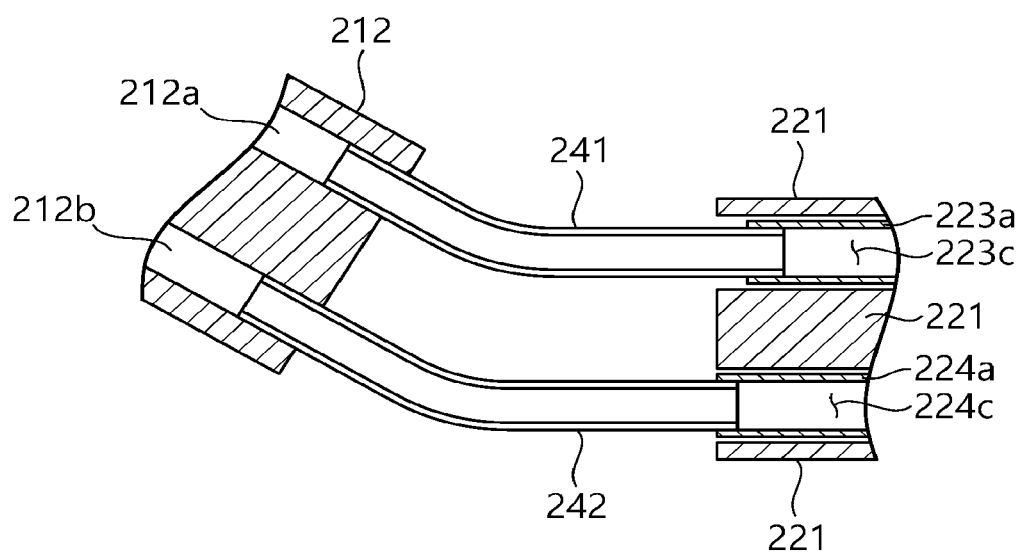
FIG. 19 is a schematic diagram illustrating the connection between a first inner body and a second inner body in an insertable device according to a third embodiment of the present invention.

FIGS. 17 and 18 are cross-sectional views of a second outer body and a second inner body in an insertable device according to a third embodiment of the present invention; and FIG. 19 is a schematic diagram illustrating the connection between a first inner body and a second inner body in an insertable device according to a third embodiment of the present invention.

In the third embodiment, the second inner body 220 further includes inserting guide (223, 224).

The inserting guide 223 includes a first inserting guide 223 and a second inserting guide 224, and thus, both inserting guides (223, 224) have the same configuration.

The first inserting guide 223 is described as follows.

The first inserting guide 223 includes a first part 223a inserted into the first guide space 221a and a second part 223b exposed to the outside, and the second part 223b has an expanded diameter compared to the first part 223a. In the first inserting guide 223, a first penetration space 223c through which a radiation source passes is formed. The first penetration space 223c is extended in the second part 223b, and the extended first penetration space 223c facilitates the insertion of a radiation source.

A user can adjust the emission direction of radiation by rotating the second part (223b, 224b) exposed to the outside.

In the third embodiment, the first accommodation guide 241 connects the first guide space 221a located at an upper part thereof and the first guide part 212a located at an upper part thereof, whereas the second accommodation guide 242 connects the second guide space 221b located at a lower part thereof and the second guide part 212b located at a lower part thereof. Specifically, the first accommodation guide 241 is connected to the first penetration space 223c and the second accommodation guide 242 is connected to the second penetration space 224c.

That is, even in the third embodiment, the connection of the accommodation guide (241, 242) is not in the form of a crossover.

In the third embodiment, in a case where a radiation source is located in the first accommodation space 211a and in a case where a radiation source is located in the second accommodation space 211b, the insertable device is configured such that the first inserting guide 223 is pushed further back than the second inserting guide 224 by the difference in length of the entire path by a rotation.

The above-described embodiments are illustrative examples for describing the present invention, and thus, the present invention is not limited thereto. Those skilled in the art to which the present invention pertains will be able to perform the present invention by various modifications therefrom, and thus, the technical protection scope of the present invention should be defined by the appended claims.

The invention claimed is:

1. A brachytherapy insertable device, comprising:
    an outer body including a first outer body extending in a long manner, a second outer body extending in a long manner, and a bent part for connecting the first outer body and the second outer body;
    a first inner body positioned inside the first outer body and having an accommodation space in which a radiation source is accommodated;
    a second inner body, which is positioned inside the second outer body, has a guide space enabling the radiation source to pass therethrough, and being capable of operating a rotation thereof; and
    an inner connection part positioned in correspondence to the bent part inside the outer body, having a connection space communicating with the guide space and the accommodation space such that the radiation source is allowed to pass therethrough, and connecting, the first inner body and the second inner body, wherein the accommodation space includes a first accommodation space and a second accommodation space having different distances from the first outer body, and the first inner body is separated from the first outer body and rotated by the rotation of the second inner body.

2. The insertable device of claim 1, wherein the first accommodation space and the second accommodation space are formed in a long manner along the first inner body.

3. The insertable device of claim 2, wherein the accommodation space is formed in a trench form within the first inner body.

4. The insertable device of claim 3, further comprising an accommodation space partitioning member positioned within the accommodation space, and the first accommodation space and the second accommodation space are separated by the accommodation space partitioning member.

5. The insertable device of claim 2, wherein the inner connection part comprises a rotation power mechanism.

6. The insertable device of claim 5, wherein the rotation power mechanism comprises at least one of a flexible shaft, a bellows, and a joint.

7. The insertable device of claim 6, wherein one end of the inner connection part is fixed to the first inner body, and an other end of the inner connection part is connected to the second inner body.

8. The insertable device of claim 2, wherein the first inner body consists of a material which has greater radiation shielding performance than the first outer body.

9. The insertable device of claim 2, wherein the guide space comprises a first guide space and a second guide space that are separated from each other, and the insertable device further comprises:

a first accommodation guide which connects the first guide space to any one of the first accommodation space and the second accommodation space within the connection space; and a second accommodation guide which connects the first guide space to the other of the first accommodation space and the second accommodation space within the connection space.

10. The insertable device of claim 9, wherein the first accommodation guide and the second accommodation guide are in a tube shape through which a radiation source is able to pass.

11. The insertable device of claim 10, wherein:

the first accommodation guide and the second accommodation guide are positioned on a periphery of the inner connection part; and the first accommodation guide is connected to either the first accommodation space or the second accommodation space, Which is positioned farther from the first guide space.

12. The insertable device of claim 10, wherein:

the inner connection part has a connection space inside;

at least part of each of the first accommodation guide and the second accommodation guide is positioned within the connection space; and the first accommodation guide is connected to either the first accommodation space or the second accommodation space, which is positioned closer to the first guide space.

13. A brachytherapy insertable device, comprising:

an outer body Which is extended lengthwise;

an inner body, which is positioned inside the outer body and has an accommodation space in which a radiation source is accommodated;

wherein the accommodation space includes a first accommodation space and a second accommodation space having different distances from the outer body, and the inner body is separated from the outer body, wherein the first accommodation space and the second accommodation space are formed along the inner body, and the inner body consists of a material which has greater radiation shielding performance than that of the outer body.

* * * * *